United States Patent
Shu

(10) Patent No.: US 8,509,972 B2
(45) Date of Patent: Aug. 13, 2013

(54) ELECTRONIC PET AND PET INTERACTION SYSTEM THEREOF

(75) Inventor: Ching-Min Shu, Taipei County (TW)

(73) Assignee: Industrial Technology Research Institute, Hsinchu (TW)

(*) Notice: Subject to any disclaimer, the term of this patent is extended or adjusted under 35 U.S.C. 154(b) by 701 days.

(21) Appl. No.: 12/486,769

(22) Filed: Jun. 18, 2009

(65) Prior Publication Data

US 2009/0265051 A1  Oct. 22, 2009

Related U.S. Application Data

(63) Continuation-in-part of application No. 11/749,754, filed on May 17, 2007, now Pat. No. 7,562,634.

(60) Provisional application No. 60/823,800, filed on Aug. 29, 2006.

(51) Int. Cl.
  *G05D 1/04* (2006.01)
  *A63H 23/10* (2006.01)
  *B63G 8/14* (2006.01)

(52) U.S. Cl.
  USPC .............................. 701/21; 114/331; 446/155

(58) Field of Classification Search
  USPC .......................................................... 700/248
  See application file for complete search history.

(56) References Cited

U.S. PATENT DOCUMENTS

| | | | | |
|---|---|---|---|---|
| 2,903,822 A | * | 9/1959 | Reid | 446/155 |
| 3,015,271 A | * | 1/1962 | MacAdams | 102/414 |
| 3,382,606 A | * | 5/1968 | Johnson | 446/198 |
| 5,477,674 A | | 12/1995 | Somers et al. | |
| 5,522,337 A | * | 6/1996 | Meyers et al. | 114/312 |
| 6,165,036 A | * | 12/2000 | Hino et al. | 446/154 |
| 6,179,683 B1 | * | 1/2001 | Pell et al. | 446/154 |
| 6,292,714 B1 | * | 9/2001 | Okabayashi | 700/245 |
| 6,698,373 B2 | | 3/2004 | Geriene et al. | |
| 6,790,119 B1 | * | 9/2004 | Chia | 446/158 |
| 6,860,785 B2 | * | 3/2005 | Vap | 446/153 |
| 6,974,356 B2 | | 12/2005 | Hobson et al. | |
| 7,007,626 B2 | | 3/2006 | Hobson et al. | |

(Continued)

FOREIGN PATENT DOCUMENTS

| CN | 1515460 | 7/2004 |
|---|---|---|
| CN | 1991692 | 7/2007 |

(Continued)

OTHER PUBLICATIONS

"First Office Action of China Counterpart Application", issued on Jul. 22, 2011, p. 1-p. 8.

(Continued)

*Primary Examiner* — Shelley Chen
(74) *Attorney, Agent, or Firm* — Jianq Chyun IP Office

(57) ABSTRACT

An electronic pet and a system therewith are provided herein. The electronic pet includes a driving device, a sensing device used to sense light, sound and contact/non-contact stimulations from an external environment, a signal transceiver device used to transceive signals to and from devices other than the electronic pet, and a processor. The pet interaction system includes an electronic pet, a system sensing device used to sense a position of the electronic pet and a physiological status of a user, a dummy, a system signal transceiver device used to transceive signals to and from the electronic pet and the dummy, and a system processor.

11 Claims, 13 Drawing Sheets

(56) References Cited

U.S. PATENT DOCUMENTS

| | | |
|---|---|---|
| 7,051,664 B2 | 5/2006 | Robichaud et al. |
| 2003/0232566 A1* | 12/2003 | Vap .......................... 446/156 |
| 2006/0000137 A1 | 1/2006 | Valdivia y Alvarado et al. |
| 2006/0234601 A1* | 10/2006 | Weston ........................ 446/268 |
| 2007/0173170 A1* | 7/2007 | Wu ............................. 446/153 |
| 2008/0053359 A1 | 3/2008 | Shu |
| 2008/0164079 A1* | 7/2008 | Jacobsen ....................... 180/7.1 |
| 2008/0281468 A1* | 11/2008 | Jacobsen et al. .............. 700/246 |
| 2009/0055019 A1* | 2/2009 | Stiehl et al. .................. 700/249 |
| 2009/0124165 A1* | 5/2009 | Weston ........................ 446/268 |
| 2010/0174422 A1* | 7/2010 | Jacobsen et al. ................. 701/2 |

FOREIGN PATENT DOCUMENTS

| | | |
|---|---|---|
| CN | 101134496 | 3/2008 |
| CN | 101322878 | 12/2008 |
| TW | 200810991 | 3/2008 |

OTHER PUBLICATIONS

"Office Action of Taiwan Counterpart Application", issued on Apr. 19, 2012, p. 1-p. 7.

* cited by examiner

ELECTRONIC PET AND PET INTERACTION SYSTEM THEREOF

CROSS-REFERENCE TO RELATED APPLICATION

This is a continuation-in-part application of patent application Ser. No. 11/749,754, filed on May 17, 2007, now allowed, which claims the benefit of U.S. Provisional Application No. 60/823,800, filed on Aug. 29, 2006, entitled "DIVING DEVICE." The entirety of the above-mentioned patent applications is hereby incorporated by reference herein and made a part of this specification.

BACKGROUND

1. Technical Field

The invention is related to an electronic pet and a pet interaction system, and particularly to an electronic pet having sensing capabilities and wireless transmission capabilities and a pet interaction system.

2. Description of Related Art

With the development of electronic technology, robots have become more popular. There are also more and more types of robots for entertainment purposes, such as the electronic pet dog AIBO by Sony, the electronic pet dog i-Cybie by Silverlit Electronics and the robot ASIMO by Honda. Such robots mostly have certain capabilities of sensing and recognition, such as position sensing, so as to coordinate actions thereof and to interact with the user or the environment. However, if such robots are to be designed for underwater usage, it is much more difficult to retain the capabilities of interacting with the user or the environment.

SUMMARY

The present invention provides an electronic pet which includes a driving device used to propel the electronic pet, a sensing device which senses light, sound contact/non-contact stimulations of the external environment and generates a sensing signal, a signal communicating device which transceives signals to and from devices other than the electronic pet. The sensing device transmits the sensing signal to the processor, the signal communicating device transmits an external device signal to the processor, and the processor processes the sensing signal and the external device signal and controls the driving device, the sensing device and the signal communicating device.

The present invention further provides a pet interaction system which includes a least an electronic pet, a system sensing device which is used to sense a position (including an angle in which a head of the electronic pet faces) of the electronic pet and a physiological status of the user and to generate a system sensing signal, a dummy which converts stimulations to the dummy into a dummy signal, a system signal communicating device, wherein the electronic pet and the dummy respectively transmit an electronic pet signal and the dummy signal to the system signal communicating device, and a system processor. The system sensing device transmits the system sensing signal to the system processor, the system signal communicating device transmits the electronic pet signal and the dummy signal to the processor, the system processor processes the system sensing signal, the electronic pet signal and the dummy signal and controls the system signal communicating device and further controls the electronic pet and the dummy through the system signal communicating device.

In order to make the aforementioned and other features and advantages of the present invention more comprehensible, several embodiments accompanied with figures are described in detail below.

In order to make the aforementioned and other features of the present invention more comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate exemplary embodiments and, together with the description, serve to explain the principles of the invention.

DESCRIPTION OF DISCLOSED EMBODIMENTS

Figure 1A:
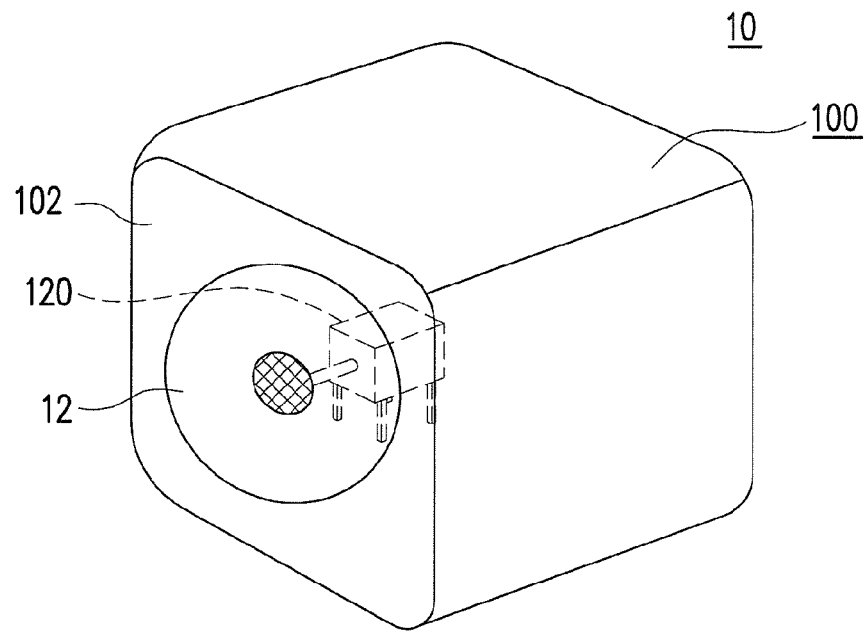
FIG. 1A is a schematic diagram of a diving device.

The capabilities to interact with the user and the environment are characteristics of an electronic pet, since without these characteristics, the mimicry ability of the electronic pet would greatly decrease and the electronic pet would not be able to bring satisfaction to the user as real pets would. Although an electronic pet in water is unique, it is difficult in terms of technology to make the electronic pet fully interact with the user and the environment. If there is an electronic pet which generates virtual emotional changes because of the touch, patting, speech or body temperature of the user or according to light, temperature or oxygen concentration of the environment, what great satisfaction would be brought to the user? The electronic pet moves with the hand of the user near the tank, moves with the user constantly, or dances with music listened by the electronic pet.

In the embodiment, it further provides an electronic pet which is adapted to an aqueous environment and for entertainment purposes.

An electronic pet is hereby developed. In addition to interaction with the user, in order to give the user a feeling of being constantly noticed by the electronic pet, the electronic pet may include a sensing device which detects a position of the user and a movement driving device to make the head of the electronic pet constantly face the user. Hence, the user feels being constantly noticed by the electronic pet. In addition to the user, the electronic pet also reacts in response to the other sounds. In addition, if the electronic pet is disposed in water, the user virtually touches the electronic pet through the dummy. Through virtual touching, the user may interact with the electronic pet more directly (for example, patting, stroking, tickling, shaking and shouting), and the electronic pet also differentiates day and night, responds to the environment (for example, light, temperature and oxygen concentration) and generates emotional responses. In order to present the emotional responses, the electronic pet may include devices to mimic real organisms, such as movable plates which are used to mimic fins or a face of a real organism.

A diving device can be applied to the embodiment of the electronic pet. The diving device is disclosed in the parent application (US Patent Publication No. 2008/0053359) which is incorporated herein by reference herewith. In the embodiment, the diving device controls floating and sinking by changing the volume of the diving device. The diving device includes a sealed main body and an actuator. The sealed main body has a flexible part which is disposed on a part of the sealed main body. Being controlled by the actuator, the flexible part may protrude or cave in, so as to change the overall volume of the diving device, thereby changing buoyancy of the diving device to make the diving device float or sink. By using the diving device, an electronic pet adapted to an aqueous environment and for entertainment purposes is designed and produced.

Figure 1B:
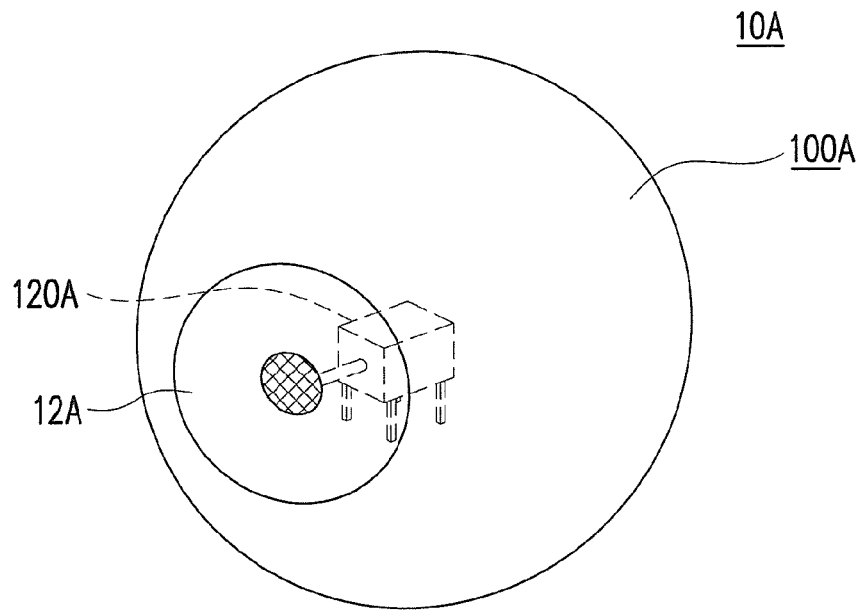
FIG. 1B is a schematic diagram of a diving device of another embodiment.

A schematic diagram of the diving device is shown in FIG. 1A. The diving device is moving in an aquarium, for example. FIG. 1A shows a lateral view of the diving device 10, which includes a sealed main body 100 with a flexible portion 12 at one part 102 of the main body 100, and an actuator 120 inside the main body 100. The actuator 120 is connected to the flexible portion 12 and pulls or pushes the flexible portion 12 so as to change the volume of the diving device. Therefore, according to the density difference between the diving device 10 and the material encompassing it, the diving device 10 moves upwards or downwards in the environment. Another embodiment is provided in FIG. 1B, which shows a schematic diagram of a diving device. In the diving device 10A, the shape of the main body 100A is spherical, and a flexible portion 12A is disposed at one part of the main body 100A. An actuator 120A is provided inside the main body 100A for pulling or pushing the flexible portion 12A.

Figure 2A:
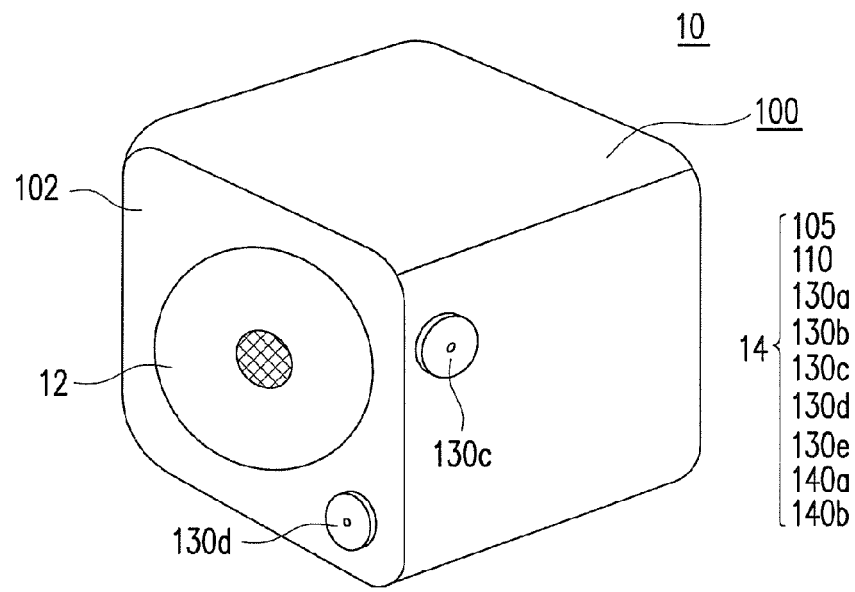
FIGS. 2A, 2B and 2C are schematic diagrams of a diving device of another embodiment.
Figure 2B:
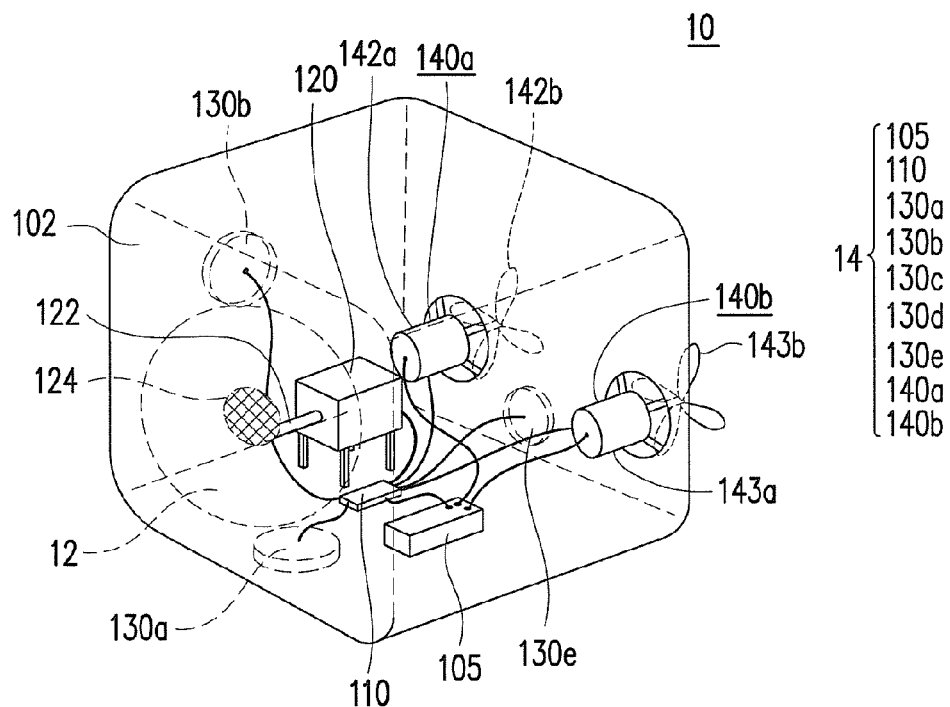
Figure 2C:
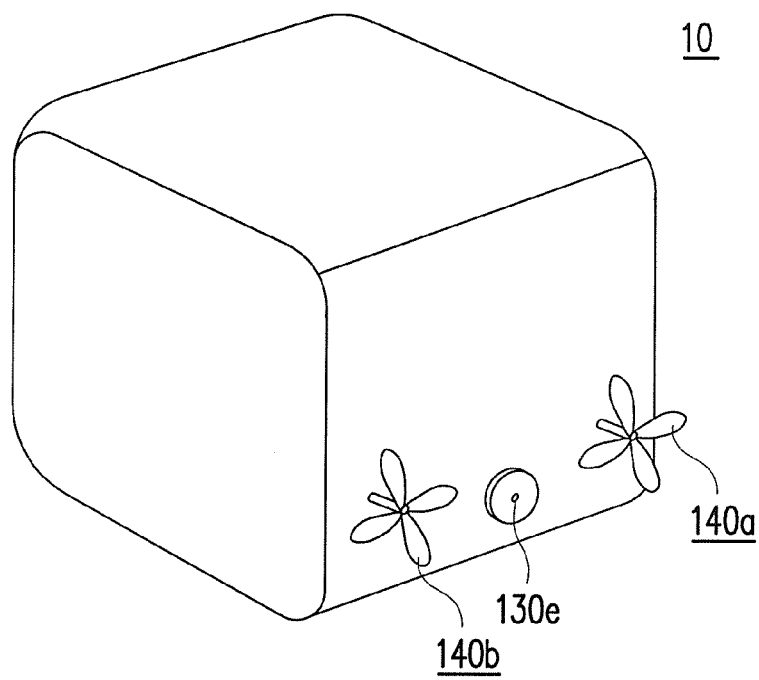

For further explanation, schematic diagrams of a diving device of another preferred embodiment of the present invention are shown in FIG. 2A, FIG. 2B and FIG. 2C. The diving device is moving in an aquarium, for example. FIG. 2A shows a lateral view of the diving device 10, FIG. 2B and FIG. 2C show perspective views of the diving device 10. The diving device 10 includes a sealed main body 100 with a flexible portion 12 at one part 102 of the main body 100, an actuator 120 inside the main body 100, and a collision avoidance system 14. The collision avoidance system 14 includes a microprocessor 110, and a power supply 105, all of which are disposed in the main body 100. The collision avoidance system 14 further includes one or a plurality of distance sensors, for example, a vertical distance sensor 130a, a pair of horizontal distance sensors 130b and 130c, a front distance sensor 130d and a rear distance sensor 130e, which are respectively disposed on different sides of the main body 100.

The collision avoidance system 14 further includes a left driving assembly 140a and a right driving assembly 140b, each of which respectively includes, for example, a motor and a propeller driven by the motor. The motors of the driving assemblies 140a and 140b are disposed in the main body 100 and the propellers of the driving assemblies 140a and 140b are disposed on one exterior side of the main body 100, as shown in FIGS. 2B and 2C. By optionally activating the left driving assembly 140a and/or the right driving assembly 140b, the forward, backward, leftward and rightward moving forces are generated, whereby the diving device 10 can move forward, backward, leftward or rightward to change the moving direction.

As shown in FIG. 2B, the actuator 120, vertical distance sensor 130a, horizontal distance sensors 130b and 130c, front distance sensor 130d and rear distance sensor 130e and driving assemblies 140a and 140b are controlled by the microprocessor 110. The actuator 120 is, for example, a servo motor, and is connected to the flexible portion 12 through a transmission shaft 122 and a connecting part 124.

By using the vertical distance sensor 130a, if a distance in a vertical direction between the diving device 10 and any other subject or the boundary is sensed to be smaller than a predetermined value, the flexible portion 12 is pushed and pulled by the actuator 120 to change volume of the diving device 10, in order to change the position of the diving device 10 to avoid collision in the vertical direction.

For example, when the vertical distance sensor 130a detects that a distance between the diving device 10 and the ground of the aquarium is larger than a predetermined value, the detecting result will be forwarded to the microprocessor 110. The microprocessor 110 will control the actuator 120 to pull the flexible portion 12 to sink inwards and the volume of the diving device 10 is decreased accordingly, and thereby the whole density of the diving device 10 is increased and a downward buoyancy force is generated to drive the diving device 10 to move downwards.

On the contrary, when the vertical distance sensor 130a detects that a distance between the diving device 10 and the ground of the aquarium is smaller than a predetermined value, the detecting result will be forwarded to the microprocessor 110. The microprocessor 110 will control the actuator 120 to push the flexible portion 12 to expand outwards and the volume of the diving device 10 is increased accordingly, and thereby the whole density of the diving device 10 is decreased and an upward buoyancy force is generated to drive the diving device to move upwards so as to prevent collision. In another example, when the horizontal distance sensors 130b or 130c detects that a distance in a horizontal direction between the diving device and any subject or the horizontal boundaries of the aquarium is smaller than a predetermined value, the detecting result will be forwarded to the microprocessor 110. The microprocessor 110 will respectively control the left driving and right driving assemblies 140a and 140b to provide power to drive the diving device moving leftward or rightward in response to the sensing result from the horizontal distance sensors 130b and 130c. The left driving assembly 140a includes a motor 142a and a propeller 142b driven by the motor 142a. The right driving assembly 140b includes a motor 143a and a propeller 143b driven by the motor 143a. The motors 142a and 143a are disposed in the main body 100 and the propellers 142b and 143b are symmetrically disposed in a left part and a right part of the same side of the main body 100.

When the front distance sensor 130d or the rear distance sensor 130e detects that a distance in the front or in the rear direction between the diving device 10 and any subject or the boundaries of the aquarium is smaller than a predetermined value, the detecting result will be forwarded to the microprocessor 110. The microprocessor 110 will respectively control the left driving and right driving assemblies 140a and 140b to provide power to drive the diving device moving backward or forward in response to the sensing result from the front distance sensor 130d and rear distance sensor 130e. For example, by activating the propeller 142b and 143b for a clockwise rotation at the same time, a power to move the diving device 10 forward is generated, and, on the contrary, if the propeller 142b and 143b are activated for a counterclockwise rotation at the same time, a power to move the diving device 10 backward is generated.

Figure 2D:
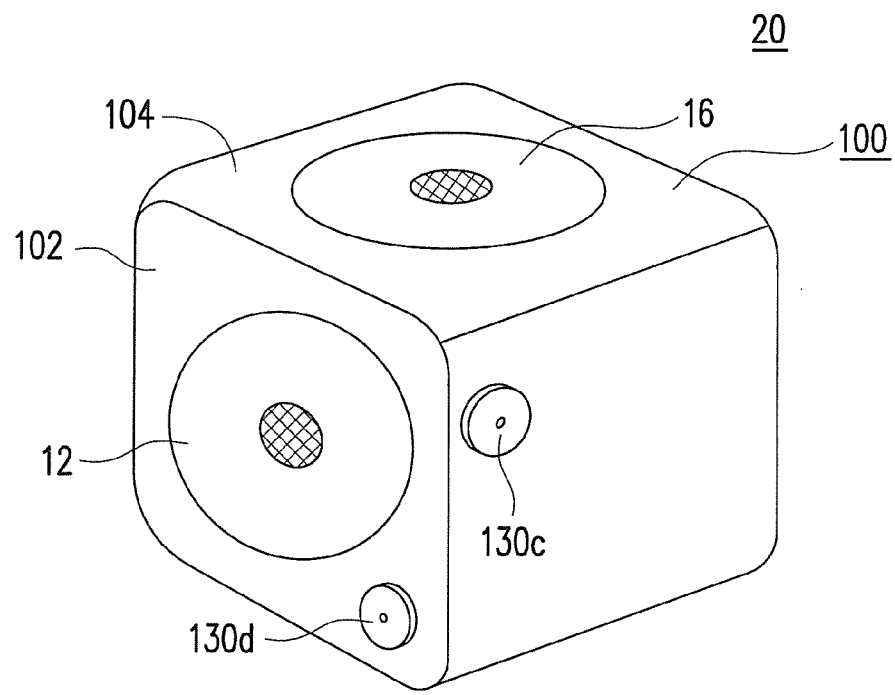
FIG. 2D is a schematic diagram of a diving device of a further embodiment.

In another embodiment, refer to FIG. 2D, which shows a schematic diagram of a diving device of another embodiment of the present invention. The diving device 20 is similar to the diving device 10 as shown in FIGS. 2A~2C except that the diving device 20 includes a sealed main body 100 with two flexible portions 12 and 16 respectively disposed on one part 102 and the other part 104 of the main body 100. The microprocessor 110 controls the actuator 120 to pull the flexible portions 12 or/and 16 to sink inwards, and the volume of the diving device 20 is decreased accordingly, and thereby the whole density of the diving device 20 is increased and a downward buoyancy force is generated to drive the diving device to move downwards. The microprocessor 110 controls the actuator 120 to push the flexible portions 12 or/and 16 to expand outwards, the volume of the diving device 20 is increased accordingly, and thereby the whole density of the diving device 20 is decreased and an upward buoyancy force is generated to drive the diving device to move upwards. It is known that more than two membranes can also be provided for the diving device 20 to generate an upward or downward buoyancy forces more efficiently, if desired.

Figure 2E:
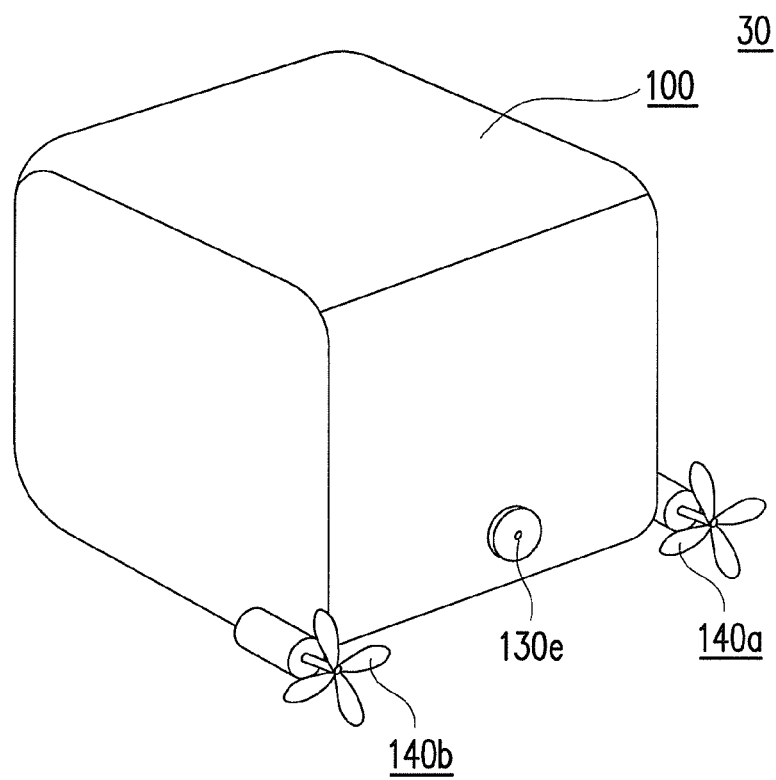
FIG. 2E is a schematic diagram of a diving device of a further embodiment.

In an alternative embodiment, refer to FIG. 2E, which shows a schematic diagram of a diving device of a further embodiment of the present invention. The diving device 30 is similar to the diving device 10 as shown in FIGS. 2A~2C except that the left driving and right driving assemblies 140a and 140b are symmetrically disposed on a left side and a right side of the main body 100. By optionally activating the left driving assembly 140a and/or the right driving assembly 140b, the forward, backward, leftward and rightward moving forces are generated, whereby the diving device can move forward, backward, leftward or rightward to change the moving direction.

The electronic pet incorporating with the idea of the aforesaid diving device is introduced hereafter.

Figure 3A:
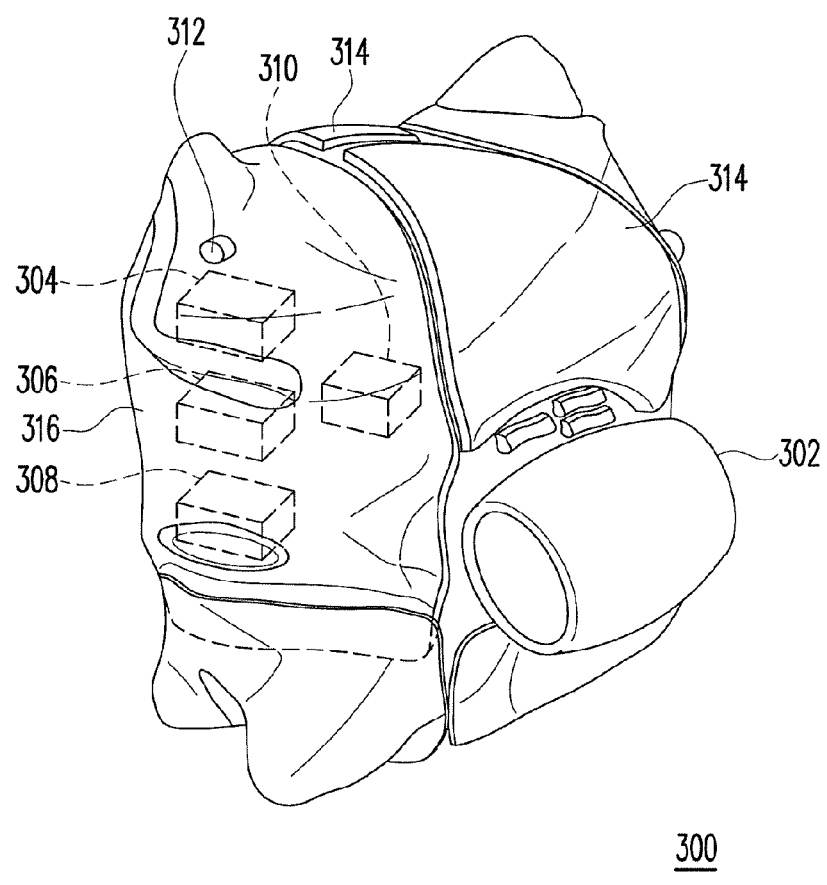
FIG. 3A is a perspective schematic view of an electronic pet according to an embodiment of the present invention.

Please refer to FIG. 3A, which is a perspective schematic view of an electronic pet according to an embodiment of the present invention. According to an embodiment of the present invention, an electronic pet 300 interacts with the user and includes a driving device 302, a sensing device 304, a signal communicating device 306, and a processor 308.

The electronic pet may, for example, include the aforesaid diving device installed therein. The sensing device 304 of the electronic pet 300 includes, for example, one of a light sensor, a sound sensor and an ultra-wide band (UWB) sensor or any combination thereof. The sensing device 304 senses environmental changes, such as changes in light and sound, and generates a sensing signal. The sensing device 304 may use light waves or sound waves to detect the positions of the user and the electronic pet, and may further use the UWB sensor to sense the physiological status of the user to detect emotions of the user. Sensing of environmental changes as described above may be adjusted according to design requirement or adjusted to comply with designs of pet interaction systems.

The signal communicating device 306 may include one of an infrared transceiver and a radio transceiver or a combination of both, for receiving and/or transmitting signals. Hence, the signal communicating device 306 receives signals to and from other devices by using the infrared transceiver or the radio transceiver and generates the external device signal.

The sensing device 304 and the signal communicating device 306 respectively transmit the sensing signal and the external device signal to the processor 308 to be processed, and the processor 308 controls the driving device 302, the sensing device 304 and the signal communicating device 306 according to the sensing signal and the external device signal or internal information, so that the signal communicating device 306 transmits signals.

According to an embodiment of the present invention, the above electronic pet 300 may be an aquatic robot. Relative designs may be referred to the aforesaid diving device. The diving device, as shown in FIG. 1A, has an exterior similar to a pet fish simulator, which is designed to be waterproof to move by floating or sinking and by using the control mechanism disclosed in aforesaid diving device.

Besides being able to further interact with the user and the environment, the electronic pet which has the exterior designed similar to a pet fish, as shown in FIG. 3A, pays attention to the user constantly. In addition to the user, the electronic pet also reacts the other sounds. In addition, if the electronic pet is disposed in water, the user virtually touches the electronic pet through the dummy. Through virtual touching, the user may interact with the electronic pet more directly (for example, patting, stroking, tickling, shaking and shouting), and the electronic pet also differentiates day and night, responds to the environment (for example, light, temperature and oxygen concentration) and generates emotional responses. Hence, according to an embodiment, the electronic pet 300 also includes at least one side plates 314 (two side plates are illustrated in FIG. 3A) and a front plate 316.

The side plates 314 and the front plate 316 are controlled by the processor 308. For example, the processor 308 controls movement of the side plates 314 according to the sensing signal and the external device signal or the internal information in the processor 308, so that the side plates 314 mimic movements of fish fins. The side plates 314 may also be moved to express emotions of happiness. The processor 308 also controls the front plate 316, so that the front plate 316 mimics a face of a real organism. For example, light is used at the front plate 316 to present a smile. The electronic pet 300 may further include a light source 312, which is also controlled by the processor 308 as the side plates 314 and the front plate 316 are, so as to emit different sorts of light in different situations. The light source 312 may include a laser light source.

Figure 3B:
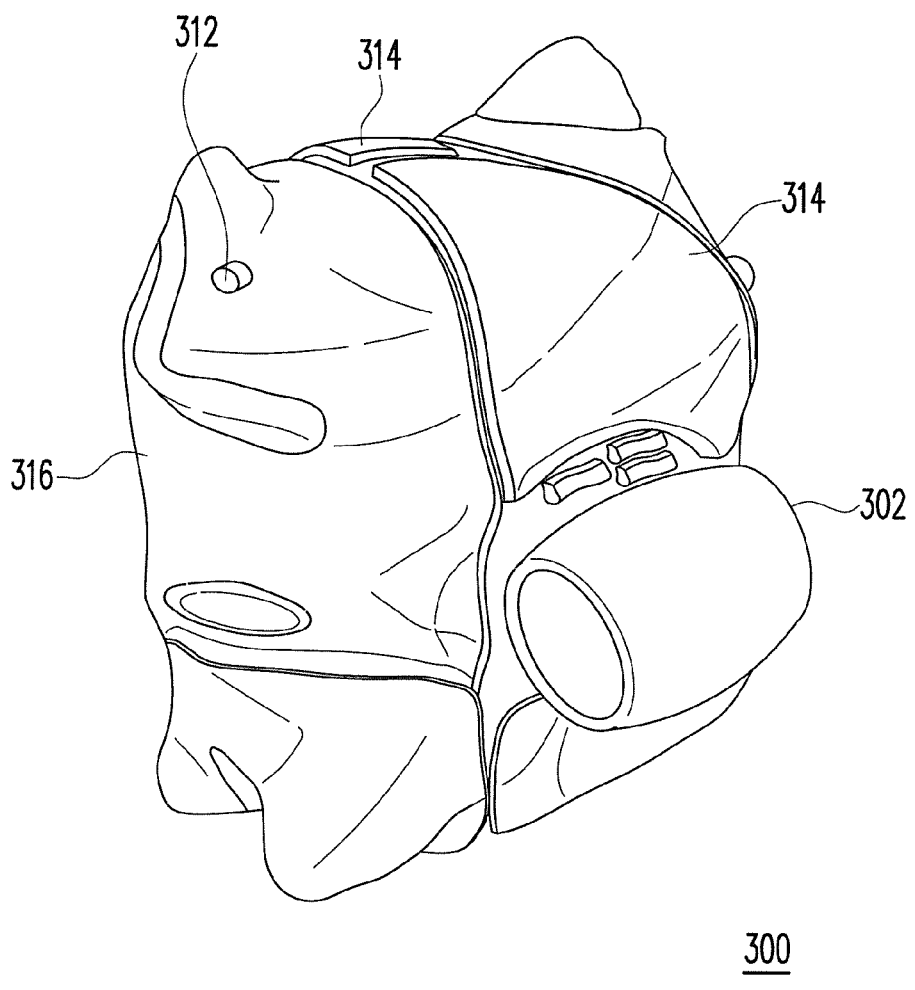
FIG. 3B is a schematic view of an electronic pet according to an embodiment of the present invention.

Please refer to FIG. 3B, which is an external schematic view of an electronic pet according to an embodiment of the present invention. Referring to FIG. 3B, it is clearly shown that the light source 312, the front plate 316 and the driving device 302 form the main part of the electronic pet 300 which is seen by the user. Hence, changes in the light source 312, the front plate 316 and the driving device 302 or even the side plates 314 clearly enable the user to feel the emotional changes presented by the electronic pet 300.

Figure 3C:
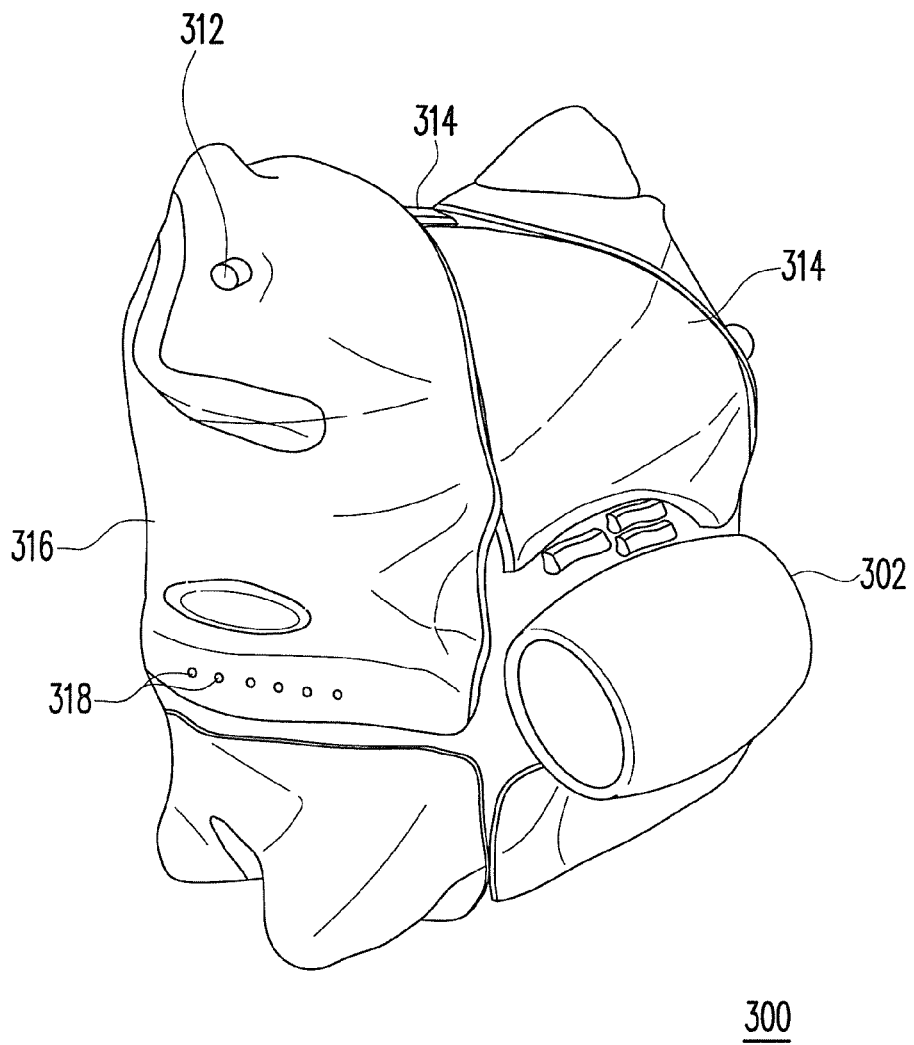
FIG. 3C is an external schematic view of an electronic pet according to an embodiment of the present invention.

Please refer to FIG. 3C, which is an external schematic view of an electronic pet according to an embodiment of the present invention. According to the present embodiment, the inside of the electronic pet 300 may further include a plurality of light-emitting devices 318. When the front plate 316 is moved, the light-emitting devices 318 are exposed. The light-emitting devices 318 are controlled by the processor 308, so as to emit different sorts of light in different situations. The light-emitting devices 318 may include a plurality of light-emitting diodes. Movement of the front plate 316 and changes in the light-emitting devices 318 enable the user to clearly feel the emotional changes presented by the electronic pet 300.

Figure 4A:
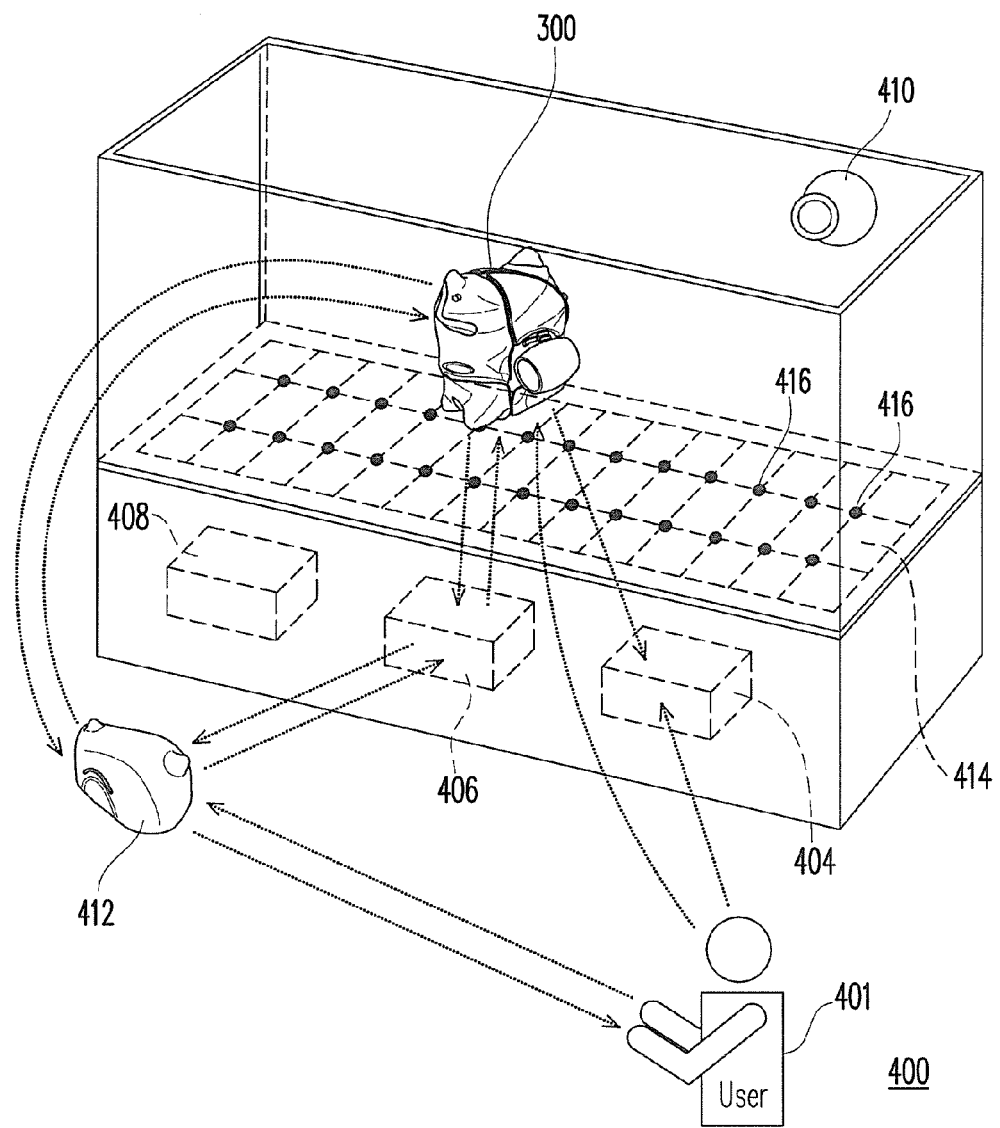
FIG. 4A is a schematic view of an electronic pet and a pet interaction system according to an embodiment of the present invention.

To enable the electronic pet 300 to be operated for a long time without being removed from the container for recharging, the electronic pet 300 may further include a non-contact charging device 310 (referring to FIG. 3A) Please refer to FIG. 4A, wherein the processor 308 controls the driving device 302 to make the charging device 310 of the electronic pet approach a non-contact charging dock 410, so as to be charged, so that the electronic pet 300 is operated in the water for a long time and is not required to be removed from water for recharging. Hence, behavior of the electronic pet is more similar to a real fish.

Figure 3D:
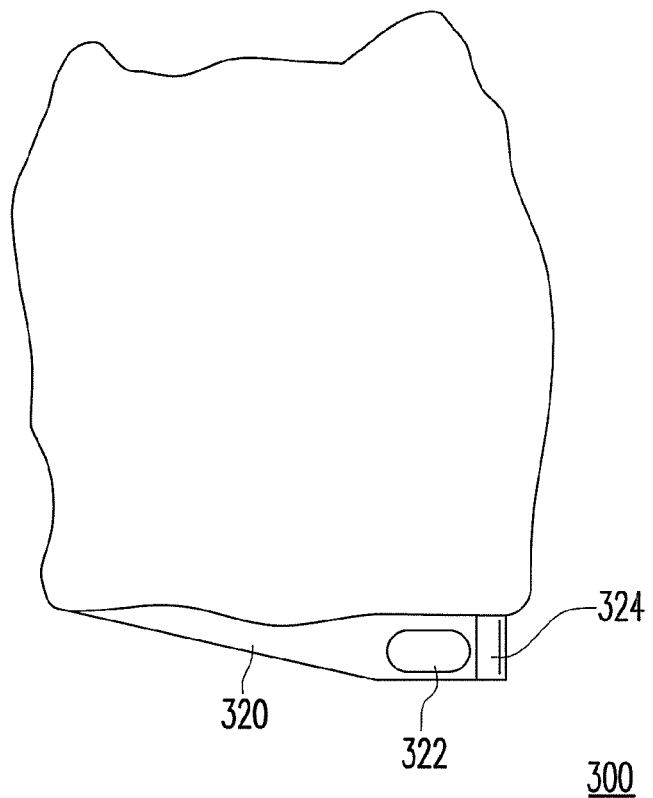
FIG. 3D is a side schematic view of an electronic pet according to an embodiment of the present invention.
Figure 3E:
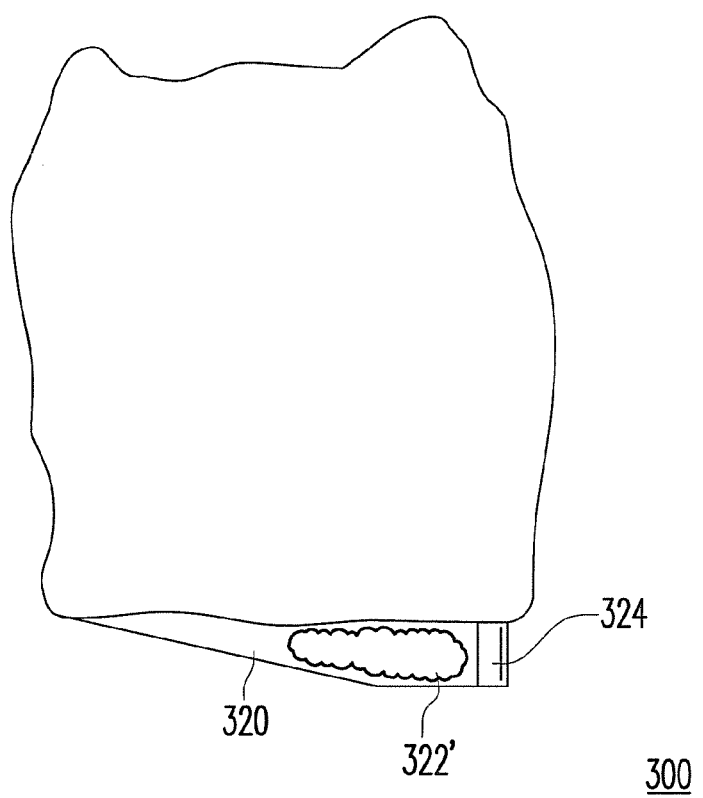
FIG. 3E is a side schematic view of an electronic pet according to an embodiment of the present invention.
Figure 3F:
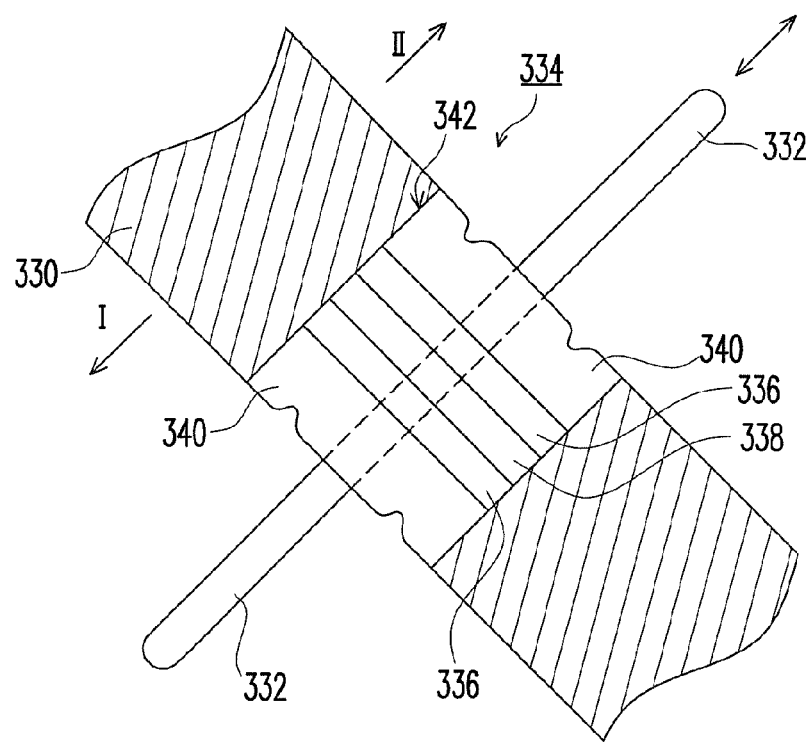
FIG. 3F, 3G are sectional schematic views of a waterproof device according to an embodiment of the present invention.

In addition, the electronic pet may further include a leakage detecting device, as shown in FIGS. 3D and 3E, each of which is a side schematic view of an electronic pet according to an embodiment of the present invention. The leakage detecting device includes a transparent chamber 320 which includes a water absorbing element 322. If leakage occurs in the electronic pet 300, the water flows to the transparent chamber 320 and is absorbed by the water absorbing element 322. After absorbing the water, the water absorbing element 322 changes into the water absorbed device 322' and swells and changes color, so that the user knows that leakage has occurred in the electronic pet 300. In addition, the transparent chamber may further include a cap 324, so that the user may replace the water absorbed device 322' through the cap.

Figure 4B:
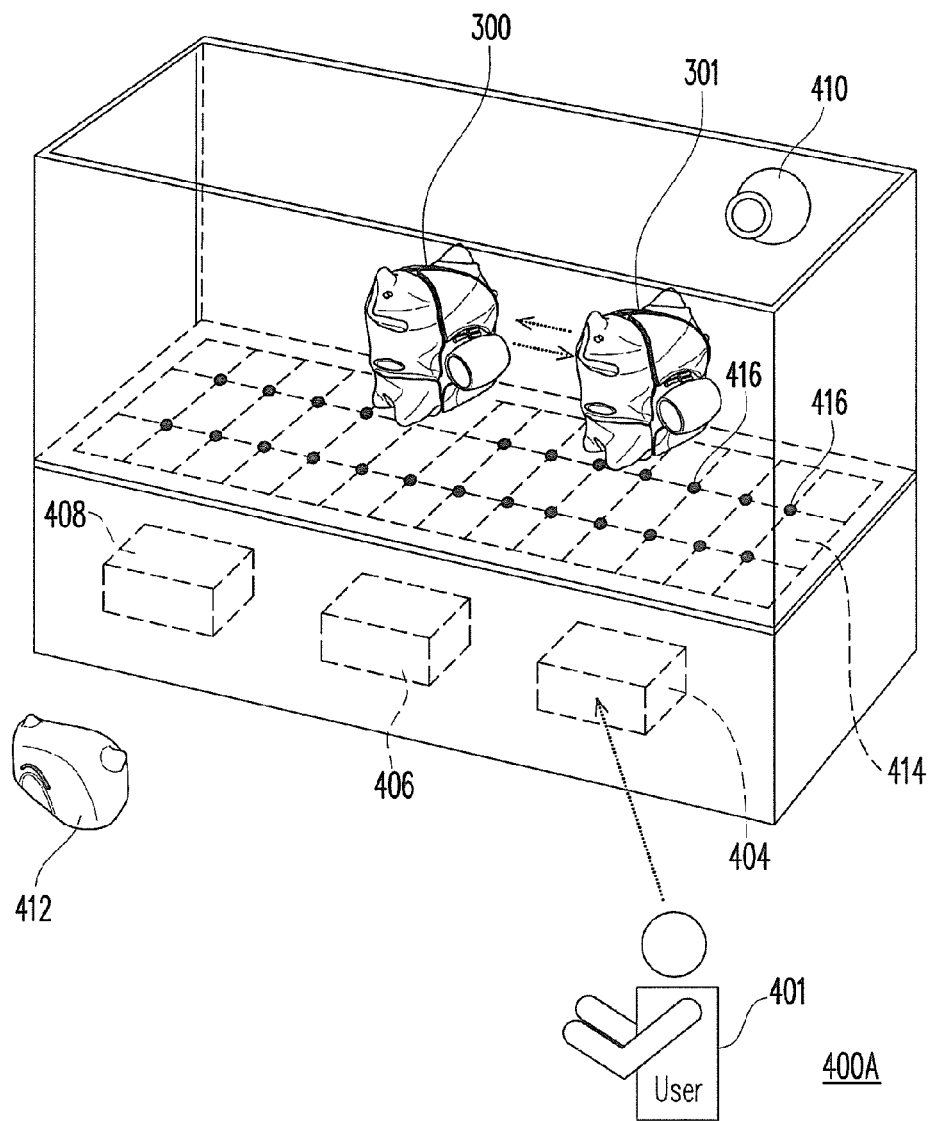
FIG. 4B is a schematic view of an electronic pet and a pet interaction system according to an embodiment of the present invention.

Moreover, the electronic pet 300 may further include a waterproof device, as shown in FIG. 4B, which is a sectional schematic view of a waterproof device according to an embodiment of the present invention. An axis 332 is used to connect a moving device inside (in a direction I) a main body housing 330 of the electronic pet 300 and a driving device outside (in a direction II) the main body housing 330 of the electronic pet 300. A waterproof device 334 is disposed on the axis 332. According to an embodiment, the waterproof device 334 includes at least two sets of bear rings 336, a waterproof material layer 338 and two sets of oil seals 340. The axis 332 and the waterproof device 334 are firmly and tightly disposed in a penetrating hole 342 of the main body housing 330, whereby a bidirectional waterproof can be achieved.

According to another embodiment, if the axis 332 is actuated in a linear direction, such as in pumping and drawing or piston motions, the waterproof device 334 may be substituted with copper sleeve bear rings or other waterproof bear rings. The above also belongs to the scope of the present invention. The driving device outside (in the direction II) described above moves, for example, the driving device 302 disposed outside the electronic pet, and may also sway the side plates 314, so that the side plates 314 mimic movements of fins of a real fish, and may control up and down movements of the front plate 316. The axis 332 may be an axis or a pull rod device of a moving device of the electronic pet 300.

The waterproof material layer 338 is, for example, oleo oil. The bear rings 336 and the waterproof material layer 338 are in close contact. In the waterproof device 334, water is insulated by the bear rings 336 and the waterproof material layer 338 in the penetrating hole, so that a side of the waterproof material layer 338 is dry while the other side is wet. The axis 332 rotates freely, and the water is insulated by the oleo oil. The axis 332, the bear rings 338 and the waterproof material layer 338 moves in a direction parallel to the axis.

Figure 3G:
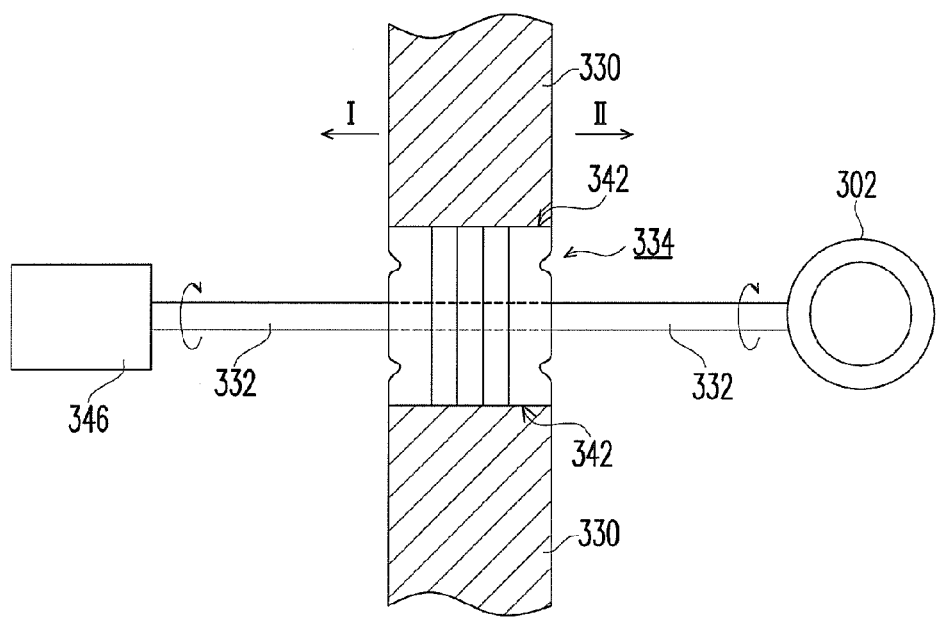

Please refer to FIG. 3G. According to an embodiment, the axis 332 is used to connect a moving device 346 inside (in the direction I) the main body housing 330 of the electronic pet 300 and a driving device, such as the driving device 302, outside (in the direction II) the main body housing 330 of the electronic pet 300. The waterproof device 334 which includes the bear rings, the waterproof material layer and the oil seal is disposed in the penetrating hole 342, and the axis 332 passes through the entire waterproof device 334, so as to prevent water outside (in the direction II) from leaking into the electronic pet 300.

Please refer to FIG. 4A, which is a schematic view of an electronic pet and a pet interaction system according to an embodiment of the present invention. The present embodiment provides a pet interaction system 400 which uses the above electronic pet 300 and is integrated into a container which houses the electronic pet, such as a tank, so as to interact with a user 401 and coordinate operations of the electronic pet 300 or a plurality of electronic pets. The pet interaction system 400 includes at least one electronic pet 300, a system sensing device 404, a system signal communicating device 406, a system processor 408 and a dummy 412. The pet interaction system 400 may further includes a board 414 and a non-contact charging dock 410.

The system sensing device 404 of the pet interaction system 400 senses a physiological status and a position of the user 401, or further senses the position of the electronic pet and generates a system sensing signal. The pet interaction system 400 includes the board 414 which is disposed at the bottom of the container and is disposed in activity region of the electronic pet 300. A plurality of sensors is disposed on the board 414, such as a plurality of sensors 416 in FIG. 4A, so as to sense the position of the electronic pet. The sensors 416 sense the current position of the electronic pet 300, or relative positions of a plurality of electronic pets 300, and transmit signals to the system sensing device 404 of the pet interaction system 400.

In order to enable to the system sensing device 404 to use light waves or sound waves to sense interaction signals of the user, or to user the UWB sensor to sense the physiological status of the user to detect his or her emotions, according to an embodiment of the present invention, the system sensing device 404 includes a light sensor, a sound sensor, a UWB sensor or any combination thereof. The sound sensor determines a direction of a sound, such as from left or from right, and reacts accordingly.

The UWB sensor adopted in the above embodiment may be the UWB non-contact sensor which uses UWB radar technology developed by the Industrial Technology Research Institute in Taiwan. The UWB non-contact sensor detects slight movement in the ribcage of the user without contacting the user, so that the UWB non-contact sensor simultaneously detects physiological statuses such as respiration and heartbeat and is commonly used for purposes of medical care. The UWB technology uses short pulse electromagnetic waves for detection, and the power is only one percent of the power of cell phone electromagnetic waves. Convenience and comfort are still maintained after long term monitoring. The UWB sensor is currently used in physiological monitoring, security, anti-collision mechanisms and positioning systems.

The pet interaction system 400 according to the present embodiment further provides a medium for interaction with the electronic pet 300 capable of operation in water. The medium is the above-mentioned dummy 412, which is used as a signal transmission device that interacts with the user 401 and the electronic pet 300 in water. The dummy 412 is similar to a remote control and converts actions imposed on the dummy 412 by the user 401, environmental changes sensed by the dummy 412 or physiological signals of sensed by the dummy 412 from the user 401 into a transmission signal. In other words, the dummy 412 converts the received stimulations into the dummy signal and directly transmits the dummy signal to the electronic pet 300 or to the system signal communicating device 406 in the pet interaction system 400, so as to interact with the user 401. The electronic pet 300 may also directly transmit the electronic pet signal to the system signal communicating device 406.

The dummy 412 includes at least one motion sensor, such as an accelerometer or a gyroscope. Actions imposed on the dummy 412 by the user 401, such as patting, stroking, shaking or talking, are converted into the dummy signal and transmitted by the dummy 412, and the method of transmitting the signal may be radio transmission or other wireless transmission methods. Besides transmitting the signal to the pet interaction system 400, the dummy 412 also responds appropriately according to the signals given by the user, for example the dummy 412 may make sounds or vibrate. In addition, the dummy 412 may also feed back signals or actions to the user according to the status of the pet interaction system 400 or the electronic pet 300. For example, when the electronic pet 300 is rapidly moving, the dummy 412 may vibrate accordingly, so that the user interacts with the electronic pet 300 in a manner that the user feels rapid movement of the electronic pet 300 through the vibration of the dummy 412.

Different from conventional remote controls, the dummy 412 may be viewed as a replica of the electronic pet. Through the various types of sensors of the dummy 412 and the signal transmissions between the dummy 412, the pet interaction system 400 and the electronic pet 300, the user feels that he or she is directly touching the electronic pet and interacting with the electronic pet. The dummy may be produced as having a same appearance as the electronic pet to achieve a greater sense of reality. In addition, the dummy 412 may include a temperature sensor, an action sensor, a light sensor, a sound sensor or any combination thereof, so as to sense the physiological status and light and sound of the environment.

The system signal communicating device 406 transmits signals between the electronic pet 300 and the dummy 412; the electronic pet and the dummy respectively transmit the electronic pet signal and the dummy signal to the system signal communicating device. The method of transmitting the signals may be radio transmission or other wireless transmissions. The system processor 408 is, for example, a core system which processes the signals from the other devices and coordinates the operations of the other devices. For example, the system sensing device 404 transmits the system sensing signal to the system processor 408, the system signal communicating device 406 transmits the electronic pet signal and the dummy signal to the processor 408, the system processor 408 processes the system sensing signal, the electronic pet signal and the dummy signal and controls the system signal communicating device 406 and further controls the electronic pet 300 and the dummy 412 through the system signal communicating device 406. The pet interaction system 400 may further include the non-contact charging dock 410, so that when the electronic pet 300 detects that it has low power, the electronic pet 300 approaches the proximity of the non-contact charging dock 410 and becomes charged.

Please refer to FIG. 4B, which is a schematic view of an electronic pet and a pet interaction system according to an embodiment of the present invention. A pet interaction system 400A shown in FIG. 4B is similar to the pet interaction system 400 shown in FIG. 4A, wherein the difference is that the pet interaction system 400A includes at least two electronic pets 300 and 301. Each of the electronic pets interacts with the user 401, the dummy 412 and the pet interaction system as illustrated above, and further interacts with other or more electronic pets.

Although the present exemplary embodiment has been described with reference to the above exemplary embodiments, it will be apparent to one of the ordinary skill in the art that modifications to the described exemplary embodiment may be made without departing from the spirit of the invention. Accordingly, the scope of the invention will be defined by the attached claims not by the above detailed descriptions.

What is claimed is:

1. A pet interaction system, comprising:
   at least an electronic pet comprising a diving device which comprises:
     a sealed main body with at least one flexible portion disposed on at least one part of the main body wherein the sealed main body is sealed from water external to the sealed main body by the at least one flexible portion together with the main body; and
     an actuator, directly connected to the flexible portion through a transmission shaft, wherein the actuator is adapted for controlling the air density of the diving device by pulling or pushing the flexible portion inwards or outwards through the transmission shaft respectively;
   a system sensing device which senses a position of the electronic pet and a physiological status of a user and generates a system sensing signal;
   a dummy converting a received stimulation or sensed signals to the dummy into a dummy signal;
   a system signal communicating device, wherein the electronic pet and the dummy respectively transmit an electronic pet signal and the dummy signal to the system signal communicating device; and
   a system processor, wherein the system sensing device transmits the system sensing signal to the system processor, the system signal communicating device transmits the electronic pet signal and the dummy signal to the system processor, the system processor processes the system sensing signal, the electronic pet signal and the dummy signal and controls the system signal communicating device and further controls the electronic pet and the dummy through the system signal communicating device.

2. The pet interaction system of claim 1, further comprising a board which comprises a plurality of sensors and is disposed under a mobile range of the electronic pet, so as to dispose the system sensing device and to sense the position of the electronic pet and the physiological status of the user.

3. The pet interaction system of claim 1, further comprising a non-contact charging dock, which is used to charge the electronic pet at a distance.

4. The pet interaction system of claim 1, wherein the system sensing device includes a light sensor, a sound sensor, a pressure sensor, an ultra-wide band sensor or any combination thereof.

5. The pet interaction system of claim 1, wherein the dummy comprises a temperature sensor, a motion sensor, a light sensor, a sound sensor, a pressure sensor, an accelerometer, a gyroscope or any combination thereof.

6. The pet interaction system of claim 1, wherein a method in which the electronic pet and the dummy respectively transmit the electronic pet signal and the dummy signal to the system signal communicating device is through radio transmission or other wireless transmissions.

7. The pet interaction system of claim 1 wherein the electronic pet comprises:

a driving device used to propel the electronic pet for movement;
a sensing device sensing light and sound of an external environment and generating a sensing signal;
a signal communicating device receiving signals from devices other than the electronic pet and generating an external device signal; and
a processor, wherein the sensing device transmits the sensing signal to the processor, the signal communicating device transmits the external device signal to the processor, and the processor processes the sensing signal and the external device signal and controls the driving device, the sensing device and the signal communicating device.

8. The pet interaction system of claim 1, wherein the density of the electronic pet is sufficiently close to the density of material encompassing the electronic pet in an environment, which makes the electronic pet being able to be floating in any position of the environment by controlling the volume of the diving device.

9. The pet interaction system of claim 1, further comprising a collision avoidance system comprising one or a plurality of sensors.

10. The pet interaction system of claim 1, wherein the driving device comprising a left driving assembly and a right driving assembly, symmetrically disposed on the electronic pet, for respectively providing power to drive the electronic pet moving forward, backward, leftward or rightward.

11. The pet interaction system of claim 10, wherein in the left driving assembly and right driving assembly, each of which includes a motor and a propeller driven by the motor.

* * * * *